(12) United States Patent
Lerner et al.

(10) Patent No.: US 7,611,722 B2
(45) Date of Patent: *Nov. 3, 2009

(54) DOSAGE FORM WITH A CORE TABLET OF ACTIVE INGREDIENT SHEATHED IN A COMPRESSED ANNULAR BODY OF POWDER OR GRANULAR MATERIAL, AND PROCESS AND TOOLING FOR PRODUCING IT

(75) Inventors: E. Itzhak Lerner, Petach Tikva (IL); Vered Rosenberger, Jerusalem (IL); Ofer Aqua, Ofra (IL); Moshe Fleshner-Barak, Petach Tikva (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 42 days.

This patent is subject to a terminal disclaimer.

(21) Appl. No.: 10/419,536

(22) Filed: Apr. 21, 2003

(65) Prior Publication Data

US 2003/0206954 A1 Nov. 6, 2003

Related U.S. Application Data

(63) Continuation of application No. 10/291,619, filed on Nov. 12, 2002, now abandoned.

(60) Provisional application No. 60/342,442, filed on Dec. 24, 2001, provisional application No. 60/361,821, filed on Mar. 4, 2002.

(51) Int. Cl.
*A61K 9/00* (2006.01)

(52) U.S. Cl. .................................................... 424/400

(58) Field of Classification Search ................. 424/472, 424/473, 474, 475, 468
See application file for complete search history.

(56) References Cited

U.S. PATENT DOCUMENTS

| 1,609,460 A | 12/1926 | Buttles |
| 3,146,169 A | 8/1964 | Stephenson et al. |
| 3,149,375 A | 9/1964 | Gehl |

(Continued)

FOREIGN PATENT DOCUMENTS

WO    WO 94/14455    7/1994

(Continued)

OTHER PUBLICATIONS

A.A. al-Quorain et al., "Non Steroidal Anti-inflammatory Drug Induced Gastropathy: a Comparative Endoscopic and Histopathological Evaluation of the Effects of Tenoxicam and Diclofenac," J. Int. Med. Res. 1993, 21(2), 89-97.

(Continued)

*Primary Examiner*—Eric E. Silverman
(74) *Attorney, Agent, or Firm*—Kenyon & Kenyon LLP

(57) ABSTRACT

A solid dosage form for oral administration to a patient comprising a core tablet sheathed in an annular body of compressed powder or granular material is provided. A preferred embodiment of the solid dosage form reduces contact of the active ingredient in solid form with the mucosa lining the gastrointestinal tract, which is particularly advantageous for delivering an ulcerative drug. A tool set comprising a columnar punch and a punch assembly comprising an annular punch and core rod, and a tableting process for making the solid dosage form are also provided.

32 Claims, 7 Drawing Sheets

U.S. PATENT DOCUMENTS

| | | | |
|---|---|---|---|
| 3,977,404 A | 8/1976 | Theeuwes | |
| 3,995,631 A | 12/1976 | Higuchi et al. | |
| 4,061,453 A | 12/1977 | DeSantis | |
| 4,382,892 A | 5/1983 | Hayakawa et al. | |
| 4,639,338 A | 1/1987 | Stahl et al. | |
| 4,839,177 A | 6/1989 | Colombo et al. | |
| 5,051,505 A | 9/1991 | Park et al. | |
| 5,053,407 A | 10/1991 | Hayakawa et al. | |
| 5,071,607 A | 12/1991 | Ayer et al. | |
| 5,074,857 A * | 12/1991 | Shepherd et al. | 604/891.1 |
| 5,088,915 A | 2/1992 | Korsch et al. | |
| 5,155,223 A | 10/1992 | Preiss | |
| 5,156,850 A | 10/1992 | Wong et al. | |
| 5,234,646 A | 8/1993 | Tanino et al. | |
| 5,256,046 A | 10/1993 | Korsch et al. | |
| 5,277,570 A | 1/1994 | Siggers | |
| 5,358,941 A | 10/1994 | Bechard et al. | |
| 5,422,123 A | 6/1995 | Conte et al. | |
| 5,425,950 A | 6/1995 | Dandiker et al. | |
| 5,431,920 A | 7/1995 | Bechard | |
| 5,462,427 A | 10/1995 | Kramer | |
| 5,498,147 A | 3/1996 | Katagiri et al. | |
| 5,539,110 A | 7/1996 | Kim et al. | |
| 5,551,856 A | 9/1996 | Katagiri | |
| 5,582,838 A | 12/1996 | Rork et al. | |
| 5,607,704 A | 3/1997 | Schlierenkämper et al. | |
| 5,635,223 A | 6/1997 | Korsch et al. | |
| 5,653,926 A | 8/1997 | Bogue et al. | |
| 5,672,364 A | 9/1997 | Kato et al. | |
| 5,681,590 A | 10/1997 | Bechard et al. | |
| 5,698,149 A | 12/1997 | Hinzmann et al. | |
| 5,804,570 A | 9/1998 | Santora, II et al. | |
| 5,882,656 A | 3/1999 | Bechard et al. | |
| 5,908,959 A | 6/1999 | Kubela et al. | |
| 5,910,324 A | 6/1999 | Koch | |
| 5,994,324 A | 11/1999 | Ashida et al. | |
| 5,994,329 A | 11/1999 | Daifotis et al. | |
| 5,994,377 A | 11/1999 | Kim et al. | |
| 6,004,120 A | 12/1999 | Matsubara et al. | |
| 6,008,207 A | 12/1999 | Brenner et al. | |
| 6,015,801 A | 1/2000 | Daifotis et al. | |
| 6,090,410 A | 7/2000 | Bechard et al. | |
| 6,113,887 A | 9/2000 | Mori et al. | |
| 6,194,004 B1 | 2/2001 | Bechard et al. | |
| 6,201,148 B1 | 3/2001 | Lidor-Hadas et al. | |
| 6,225,294 B1 | 5/2001 | Daifotis et al. | |
| 6,264,985 B1 * | 7/2001 | Cremer | 424/473 |
| 6,281,381 B1 * | 8/2001 | Finkelstein et al. | 562/13 |
| 6,358,970 B1 | 3/2002 | Duggan et al. | |
| 6,399,592 B1 | 6/2002 | Whiteford | |
| 6,406,714 B1 | 6/2002 | Bechard et al. | |
| 6,413,955 B1 | 7/2002 | Askew et al. | |
| 6,414,006 B1 | 7/2002 | Harada et al. | |
| 6,416,737 B1 | 7/2002 | Manolagas et al. | |
| 6,432,931 B1 | 8/2002 | Reszka et al. | |
| 6,465,017 B1 | 10/2002 | Tomer et al. | |
| 6,476,006 B2 | 11/2002 | Flashner-Barak et al. | |
| 6,544,967 B2 | 4/2003 | Daifotis et al. | |
| 6,562,974 B2 | 5/2003 | Cazer et al. | |
| 6,573,401 B1 | 6/2003 | Bosch i Lladóet al. | |
| 6,586,457 B2 | 7/2003 | Harada et al. | |
| 6,620,358 B2 | 9/2003 | Voss | |
| 6,623,755 B2 | 9/2003 | Chen et al. | |
| 6,627,221 B2 | 9/2003 | Gabel et al. | |
| 6,645,974 B2 | 11/2003 | Hutchinson et al. | |
| 6,696,601 B2 | 2/2004 | Finkelstein et al. | |
| 6,863,901 B2 | 3/2005 | Hirsh et al. | |
| 6,924,389 B2 | 8/2005 | Jackstell et al. | |
| 6,963,008 B2 | 11/2005 | Finkelstein et al. | |
| 7,009,071 B2 | 3/2006 | Dabak et al. | |
| 7,038,083 B2 | 5/2006 | Lidor-Hadas et al. | |
| 7,112,577 B2 | 9/2006 | Hamied et al. | |
| 2001/0036475 A1 | 11/2001 | Chen et al. | |
| 2001/0051616 A1 | 12/2001 | Karpf et al. | |
| 2002/0052527 A1 | 5/2002 | Lidor-Hadas et al. | |
| 2002/0151459 A1 | 10/2002 | Bergstrom et al. | |
| 2002/0169148 A1 | 11/2002 | Yates | |
| 2003/0032629 A1 | 2/2003 | Daifotis et al. | |
| 2003/0203878 A1 | 10/2003 | Flashner-Barak et al. | |
| 2005/0026871 A1 | 2/2005 | Flashner-Barak et al. | |
| 2005/0113343 A1 | 5/2005 | Sienkiewicz et al. | |
| 2005/0113602 A1 | 5/2005 | Kessinger et al. | |
| 2005/0181043 A1 | 8/2005 | Nandi et al. | |
| 2005/0256334 A1 | 11/2005 | Welz-Biermann et al. | |
| 2005/0288509 A1 | 12/2005 | De Ferra et al. | |

FOREIGN PATENT DOCUMENTS

| | | |
|---|---|---|
| WO | WO 96/19201 | 6/1996 |
| WO | WO 98/23263 | 6/1998 |
| WO | WO 98/56360 | 12/1998 |
| WO | WO 00/04924 | 2/2000 |
| WO | WO 00/49026 | 8/2000 |
| WO | WO 03/007916 | 1/2003 |
| WO | WO 03/057136 | 7/2003 |
| WO | WO 03/064438 | 8/2003 |
| WO | WO 03/093282 | 11/2003 |
| WO | WO 03/097655 | 11/2003 |
| WO | WO 2005/035542 | 4/2005 |

OTHER PUBLICATIONS

P.M. Goggin et al., "Prevalence of *Helicobacter Pylori* Infection and its Effect on Symptoms and non-Steroidal Anti-inflammatory Drug Induced Gastro-intestinal Damage in Patients with Rheumatoid Arthritis," Gut 1993, 34(12), 1677-80.

M. Frezza et al., "The Histopathology of Non-Steroidal Anti-inflammatory Drug Induced Gastroduodenal Damage: Correlation with *Helicobacter Pylori*, Ulcers and Haemorrhagic Events," J. Clin. Pathol. 2001, 54(7), 521-5.

K.O. Larsen, "Oesophagusskader Relatert til Bisfosfonater," Tidsskr. Nor. Lægeforen 2000, 120(2), 2397-9.

D.Y. Graham et al., "Alendronate and Naproxen Are Synergistic for Development of Gastric Ulcers," Arch. Intern. Med. 2001, 161(1), 107-110.

F.L. Lanza et al., "Endoscopic Comparison of Esophageal and Gastroduodenal Effects of Risedronate and Alendronate in Postmenopausal Women," Gastroenterology 2000, 119(3), 631-8.

D.C. Bauer et al., "Upper Gastrointestinal Tract Safety Profile of Alendronate: the Fracture Intervention Trial," Arch. Intern. Med. 2000, 160(4), 517-25.

J.K. Marshall et al., "A Randomized Controlled Trial to Assess Alendronate-associated Injury of the Upper Gastrointestinal Tract," Aliment. Pharmacol. Ther. 2000, 14(11), 1451-7.

D.Y. Graham et al., "Alendronate Gastric Ulcers," Aliment. Pharmacol. Ther. 1999, 13(4), 515-9.

S.C. Abraham et al., "Alendronate-associated Esophageal Injury:pathologic and Endoscopic Features," Mod. Pathol. 1999, 12(12), 1152-7.

S.N. Elliott et al., "Alendronate Induces Gastric Injury and Delays Ulcer Healing in Rodents," Life Sci. 1998, 62(1), 77-91.

D.Y. Graham, "Excess Gastric Ulcers are Associated with Alendronate Therapy," Am. J. Gastroenterol. 1998, 93(8), 1395-6.

R.E. Colina et al., "A New Probable Increasing Cause of Esophageal Ulceration: Alendronate," Am. J. Gastroenterol. 1997, 92(4), 704-6.

D. Jasperson, "Drug Induced Oesophageal Disorders:pathogenesis, Incidence, Prevention and Management," Drug Saf. 2000, 22(3), 237-249.

S.J. Smith et al., "Pill-induced Esophagitis Caused by Oral Rifampin," Ann.Pharmocother. 1999, 33(1), 27-31.

J.W. Kikendall, "Pill Esophagitis," J. Clin. Gastroenterol. 1999, 28(4), 298-305.

A. Minocha et al., "Pill Esophagitis Caused by Non-steroidal Antiinflammatory Drugs," Am. J. Gasterenterol. 1991, 86(8), 1086-9.

A.C. Perkins et al., "The Use of Scintigraphy to Demonstrate the Rapid Esophageal Transit of the Oval Film-coated Placebo Risedronate Tablet Compared to a Round Uncoated Placebo Tablet When Administered with Minimal Volumes of Water," Int. J. Pharm, 2001, 222(2) 295-303.

V. Simko et al., "Increased Risk in Esophageal Obstruction with Slow Release Medications," J. Assoc. Acad. Minor. Phys., 1997, 8(2), 38-42.

Physicians' Desk Reference 58th Edition. Thomson PDR p. 1986 (2004).

P. Laidler et al. "What's New in Osmosin and Intestinal Perforation?", Pathology Research and Practice, vol. 180, No. 1, pp. 74-76, 1985.

* cited by examiner

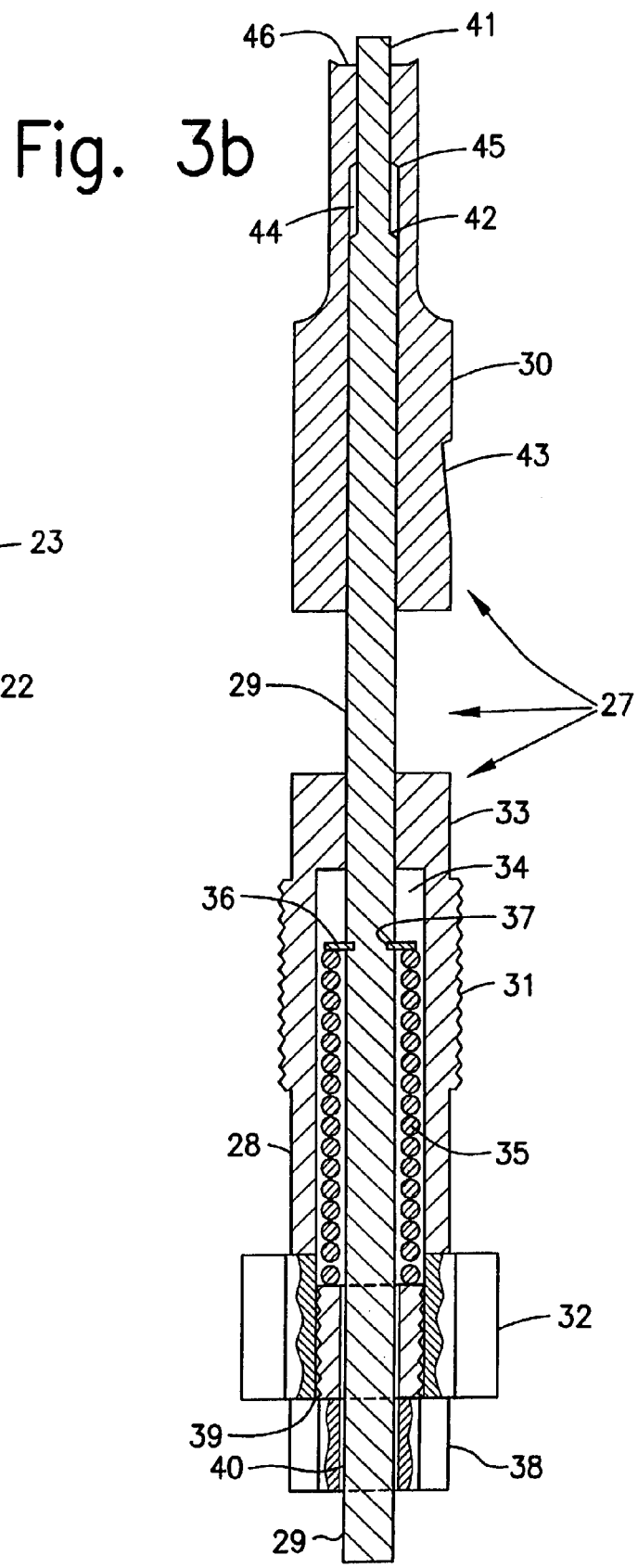

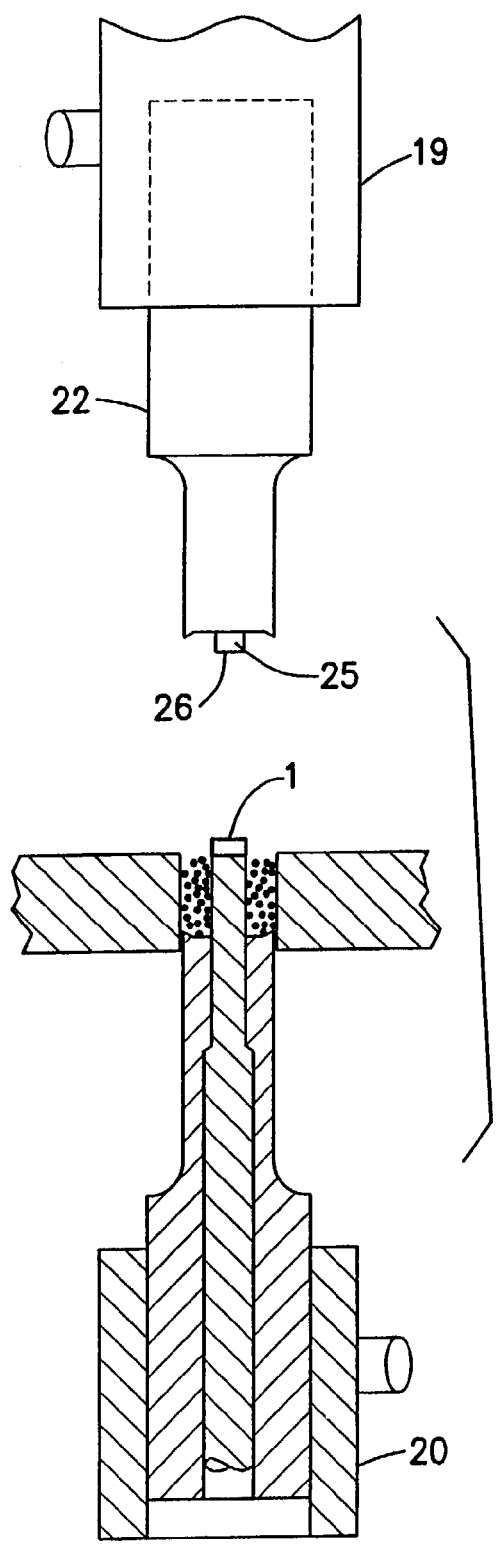
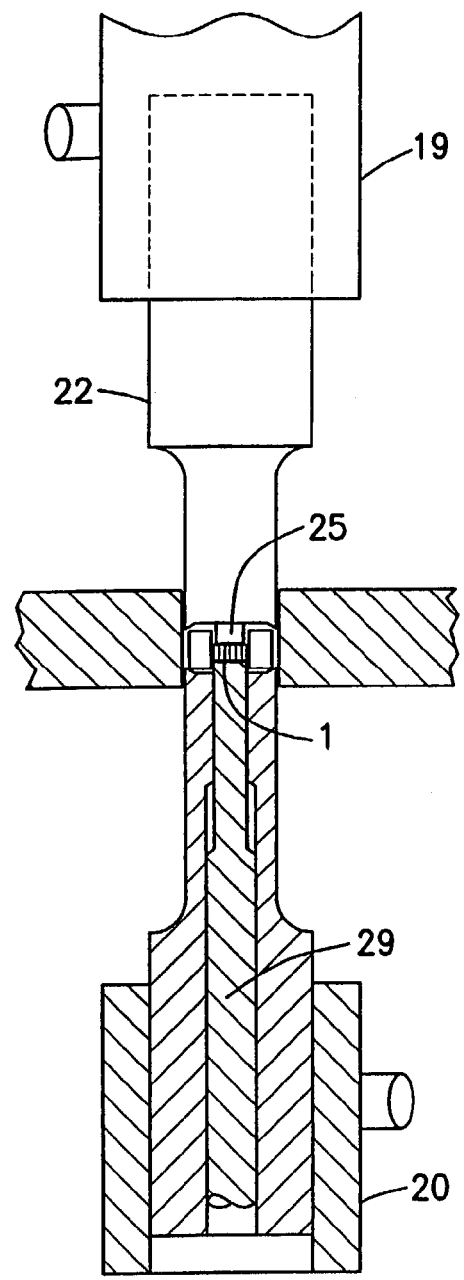
Fig. 4c
Fig. 4d

DOSAGE FORM WITH A CORE TABLET OF ACTIVE INGREDIENT SHEATHED IN A COMPRESSED ANNULAR BODY OF POWDER OR GRANULAR MATERIAL, AND PROCESS AND TOOLING FOR PRODUCING IT

CROSS-REFERENCE TO RELATED APPLICATIONS

This application is a continuation of U.S. patent application Ser. No. 10/291,619, now abandoned, filed Nov. 12, 2002, which claims the benefit of provisional application Serial No. 60/342,442, filed Dec. 24, 2001, and provisional application Serial No. 60/361,821, filed Mar. 4, 2002, all of which are incorporated herein by reference.

FIELD OF THE INVENTION

The present invention relates to powder molding, pharmaceutical dosage forms, tableting processes and equipment, and improved solid dosage forms for oral delivery of drugs that cause contact irritation or ulceration to the lining of the esophagus and stomach.

BACKGROUND OF THE INVENTION

Gastrointestinal side effects are a common and serious problem with many drugs. These side effects may manifest themselves in nausea or diarrhea or with injury to the gastrointestinal mucosa. Many drugs have been shown to cause damage to the mucosal lining of the esophagus (esophagitis) or the stomach (gastritis). Among the drugs known to cause such damage are non-steroidal anti-inflammatory drugs ("NSAIDs"). See A. A. al-Quorain et. al., "Non Steroidal Anti-inflammatory Drug Induced Gastropathy", *J. Int. Med. Res*. 1993, 21(2), 89-97; P. M. Goggins et. al., "Prevalence of Heliobacter Pylori Infection and its Effect on Symptoms and non-Steroidal Anti-inflammatory Drug Induced Gastro-intestinal Damage in Patients with Rheumatoid Arthritis" *Gut*, 1993, 34(12), 1677-80 ; M. Frezza et. al., "The Histopathology of Non-Steroidal Anti-inflammatory Drug Induced Gastroduodenal Damage: Correlation with Heliobacter Pylori, Ulcers and Haemorrhagic Events" *J. Clin. Pathol*. 2001, 54(7), 521-5 and references therein. Other drugs known to cause such damage are bisphosphonates. See K. O. Larsen, "Oesophagusskader Relatert till Bisphosphonater" *Tidsskr. Nor. Laegeforen* 2000, 120(20), 2397-9; D. Y. Graham, H. M. Malaty, "Alendronate and Naproxen Are Synergic for Development of Gastric Ulcers" *Arch. Inter. Med*. 2001, 161(1), 107-110; F. L. Lanza et. al., "Endoscopic Comparison of Esophageal and Gastroduodenal Effects of Risedronate and Alendronate in Postmenopausal Women" *Gastroenterology*, 2000, 119(3), 631-8.

In the case of NSAIDs, bisphosphonates and many other drugs, there is much evidence to implicate the solid form of the drug in causing esophagitis and gastritis. See D. Jasperson, "Drug Induced Esophageal Disorders:pathnogenesis, Incidence, Prevention and Management" *Drug Saf.* 2000, 22(3), 237-249; S. J. Smith et al., "Pill-induced Esophagitis Caused by Oral Rifampin" *Ann. Pharmocother*. 1999, 33(1), 27-31; J. W. Kikendall, "Pill Esophagitis" *J. Clin. Gastroenterol*. 1999, 28(4), 298-305; A. Minchoa, D. S. Greenbaum, "Pill Esophagitis Caused by Non-steroidal Antiinflammatoy Drugs" *Am. J. Gasterenterol*., 1991, 86(8), 1086-9. Such esophagitis is called pill induced esophagitis or pill esophagitis and when causing damage to the stomach lining can be called contact gastritis. These forms of mucosal damage can be mitigated by preventing the physical contact of the drug containing solid dose formulation with the surface of the mucosa.

Pill esophagitis and contact gastritis can be reduced by limiting physical contact between the pill containing the drug and the mucosal lining. Solutions suggested in the literature include coatings to limit esophageal contact, coatings to shorten esophageal transit time and improvements in tablet shape to shorten esophageal transit time. See A. C. Perkins et. al., "The Use of Scintigraphy to Demonstrate the Rapid Esophageal Transit of the Oval Film-coated Placebo Risendronate Tablet Compared to a Round Uncoated Placebo Tablet When Administered with Minimal Volumes of Water" *Int. J. Pharm*., 2001, 222(2) 295-303; T. S-H. Chen, U.S. patent application Ser. No. 2001/0036475; A. G. Daifotis et. al., U.S. Pat. No. 5,994,329 (enteric coatings and film coatings through which the drug is released). Each of these methods has a drawback. Coatings that come off in the stomach may be removed earlier than planned while in the esophagus leading to esophagitis. Furthermore, such coatings will not prevent gastritis. Coatings or shape improvements that shorten esophageal transit time can help prevent esophagitis but again not gastritis. Enteric coatings can totally envelope the pill until it is in the small intestine. While this can prevent contact esophagitis or gastritis it will not protect against ulceration in the small intestine and will not be desired for a drug whose absorption site is in the upper part of the GI tract (stomach or duodenum).

A further suggestion to prevent contact between the solid particles of the drug formulation and the mucosal lining is to encapsulate the drug totally in a capsule or coating and release the drug slowly through an orifice or through the film coat by diffusion or through micropores. These suggestions can be fulfilled by using an osmotic pump device to deliver the drug or a permeable film coat such as Eudragit NE or Eudragit RL or RS. The osmotic pump idea is not a promising solution to the problem of contact esophagitis and gastritis. While the drug leaves the osmotic pump in solution in most cases, the osmotic agents themselves are ulcerative in high concentrations. The stream of drug plus osmotic agent leaving the orifice causes ulceration, especially if the device has lodged against the mucous membrane See V. Simko et. al., "Increased Risk in Esophageal Obstruction with Slow Release Medications" *J. Assoc. Acad. Minor. Phys*., 1997, 8(2), 38-42. A permeable film coat can serve as a solution to the problem but it limits the drug release profile attainable since only relatively slower release profiles will be obtained and immediate release, or very short slow release profiles are not compatible with the film coat.

In view of the foregoing, it would be highly desirable to have a versatile solid dosage form that reduces contact between the lining of the gastrointestinal tract and a drug contained in the dosage form, particularly an ulcerative drug. Accordingly, one object of the present invention is to provide a solid dosage form that can release a drug according to a predetermined release profile and reduce contact of the solid drug with the lining of the gastrointestinal tract during transit of the dosage form through the esophagus, stomach and intestine.

A novel set of tooling and tableting process have been invented to produce a dosage form meeting the foregoing stringent requirements on tableting presses that are presently available from commercial sources. Tableting presses are well known and available in many designs, and with an array of features. Some presses with high throughput capacity are designed for large production runs. Others are adapted for application of compression coatings, production of multilayer tablets or engraving. Design features which are desirable in presses to be used with the novel toolset of this invention will become apparent from consideration of the detailed description of the preferred embodiments of the invention which follows.

U.S. Pat. No. 5,071,607 describes a pair of dies (punches) with piercing means biased into a sheathed position, which, when used to compress a coating about an object, pierce the object. The punches are adapted for piercing an osmotic drug dispensing vehicle. The piercing means are integral to the punches. They are moved from a sheathed to an unsheathed position by compressive force from punch actuators. Being integral with the punches, the piercing means are not capable of motion or stasis independent of the motion of the punches.

U.S. Pat. No. 3,146,169 describes a tablet comprising a medicated portion and a non-medicated inert portion of sublimed sulfur, plastic, bone phosphate, barium sulfate, wax, calcium silicate and or aluminum silicate which covers part but not all of the surface of the medicated portion. The function of the inert portion is to expose to the gastric fluids only a portion of the surface of the medicated portion (through a single hole in the inert portion) so as to slow the rate of release relative to a conventional tablet and maintain the rate of release constant. The tablet is made by feeding the space between the upper and lower punch faces of a compression coating machine successive batches of material; first, granules of inert material; second, a preformed core of the medicated material; and third, more granules of the inert material. The upper punch face is provided with a protrusion so that when the punch faces are brought together the inert material is compressed around the inner medicated core in the form of a layer provided with a hole made by the protrusion on the upper punch face. The protrusion is pointed and forms a single hole in the medicated portion as well as the inert portion.

U.S. Pat. No. 5,551,856 describes an apparatus for connecting an assembly of three concentrically aligned movable punches which are independently actuated by hydraulic means to a main body of a pressing machine.

In view of the foregoing, there is a need for a versatile solid dosage form that reduces contact between the mucosa lining the gastrointestinal tract and a solid drug contained in the dosage form and equipment and a process for producing such a dosage form.

SUMMARY OF THE INVENTION

One object of the invention is to provide a novel solid dosage form for oral administration to a patient wherein the active ingredient is contained in a core tablet that is sheathed in a compressed annular body of powder or granular material formed around the core tablet by compression.

Another object of the invention is to provide a solid dosage form for oral administration to a patient that reduces contact between the mucosa lining the gastrointestinal tract and a solid drug contained in the dosage form. In satisfaction of this object there is provided a preferred embodiment of the solid dosage form in which the core tablet is recessed in the annular body to shield it from contact with the mucosa lining the gastrointestinal tract. The solid dosage form is well suited for oral delivery of ulcerative active ingredients like bisphosphonates and NSAIDs. In an especially preferred dosage form embodiment, the annular body has opposed annular faces that are aligned substantially coaxially with recessed opposing surfaces of the core tablet. The opposed surfaces of the core tablet are substantially exposed to the external environment and drug release occurs from the exposed surfaces.

In a second dosage form embodiment, which is suitable for use with non-ulcerative drugs, the opposed surfaces of the core tablet are not recessed. Rather, they are flush with the annular faces of the annular body.

Another object of the invention is to provide a toolset that can be used with commercially available tableting presses to make the solid dosage forms of the invention. The toolset comprises a generally columnar punch having a contact face for pressing against a powder or granular material. The contact face has a protrusion near its center if the upper punch is to be used to make a compacted dosage form with a recessed core tablet. The toolset further comprises a punch assembly comprising an annular punch and a core rod slidably engageable with the annulus of the annular punch and capable of movement between a retracted position and an extended position, the core rod being biased in an extended position when the toolset is in use.

Yet another object of the invention is to provide a process for making the solid dosage forms of the invention. In its particulars, the process comprises filling an annular cavity defined by a die bore, the core rod and the contact face of the annular punch with a powder or granular material, positioning a core tablet atop the tip of the core rod and advancing the columnar punch into the die bore.

The columnar punch pushes the core tablet into the die bore against the bias force exerted by the core rod. If the columnar punch is equipped with a protrusion, the protrusion pushes the core tablet into the die. Otherwise, the contact surface of the columnar punch pushes the core tablet into the die bore. As the core tablet is pushed into the die bore, the core rod retracts against the bias force. Meanwhile, the action of the columnar punch compresses the powder or granular material into an annular body around the core tablet.

The process further comprises withdrawing at least one of the punches from the bore and ejecting the finished dosage form, such as withdrawing the columnar punch and advancing the annular punch to eject the dosage form.

BRIEF DESCRIPTION OF THE FIGURES

FIG. 3 is a sectional side view of the columnar punch and punch assembly.

FIGS. 4a-4e are sectional side views depicting stages in a cycle of operation from delivery of powder or granular material to ejection of a finished tablet at a tableting station equipped with a toolset in accordance with the invention.

DESCRIPTION OF THE PREFERRED EMBODIMENTS

Figure 1A:
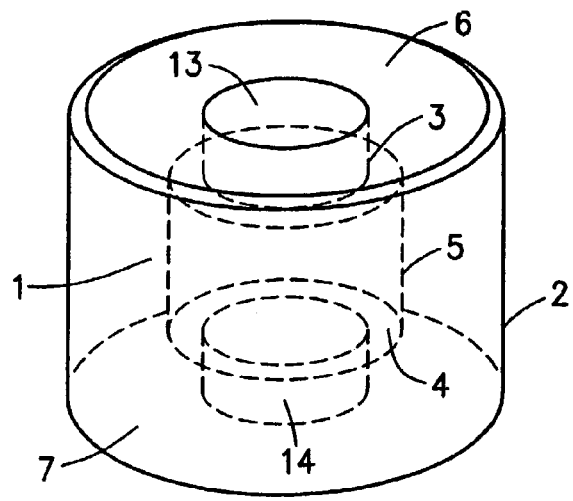
FIG. 1 shows sectional perspective, side and top down views of a solid dosage form with a recessed core tablet of active ingredient in a compressed annular body of powder or granular material in accordance with the invention.

The present invention provides a novel solid dosage form, as well as tooling and a process for producing the novel dosage form. Preferred embodiments of the invention are well suited for the administration of ulcerative drugs. As used in this disclosure, the term "ulcerative" in reference to an active pharmaceutical ingredient, drug or excipient means that when the drug or excipient is contacted as a solid with the mucosa lining at least a portion of the gastrointestinal tract it causes erosive damage. Alendronate, other bisphosphonates and NSAIDS that non-selectively inhibit the COX-1 and COX-2 enzyme are ulcerative drugs.

The novel dosage form comprises a core tablet containing an active pharmaceutical ingredient sheathed in an annular body comprised of compressed powder or granular material. The core tablet has first and second opposed surfaces and a circumferential surface. "Sheathing" means that the annular body encircles the core tablet and is in contact with the core tablet about its circumferential surface, but leaves opposed surfaces of the core tablet substantially exposed. The core tablet contains at least one active pharmaceutical ingredient, but otherwise its formulation is not critical to the invention. The core tablet can be formulated for any desired release profile, such as immediate release, delayed release, burst or pulsed release, sustained or zero order release. The annular body can be formulated to achieve any desired purpose, such as gastric retention, ease of swallowing, taste masking and control of the rate of drug release from the core tablet. The annular body also can contain or be coated with a co-active ingredient.

The type of drug to be delivered also is not an essential element of the invention. The terms "drug" and "active pharmaceutical ingredient" broadly include any biologically, physiologically, or pharmacologically active the agent. Active pharmaceutical ingredients that can be administered in the compressed dosage form of the present invention include adrenergic receptor agonists and antagonists; muscarinic receptor agonists and antagonists; anticholinesterase agents; neuromuscular blocking agents; ganglionic blocking and stimulating agents; sympathomimetic drugs; serotonin receptor agonists and antagonists; central nervous system active drugs such as psychotropic drugs, antipsychotic drugs, antianxiety drugs, antidepressants, antimanic drugs, anesthetics, hypnotics, sedatives, hallucinogenic drugs and antihallucinogenic drugs; antiepileptic drugs; antimigraine drugs; drugs for treatment of Parkinson's, Alzheimer's and Huntington's disease; analgesics; antitussive agents; antihistaminic drugs; $H_1$, $H_2$, and $H_3$ receptor antagonists; bradykinin receptor antagonists; antipyretic agents; antiinflammatory agents; NSAIDs; diuretics; inhibitors of $Na^+$-$Cl^-$ symport; vasopressin receptor agonists and antagonists; ACE inhibitors; angiotensin II receptor antagonists; renin inhibitors; calcium channel blockers; β-adrenergic receptor antagonists; antiplatelet agents; antithrombic agents; antihypertensive agents; vasodialators; phosphodiesterase inhibitors; antiarrhythmic drugs; HMG CoA reductase inhibitors; $H^+$, $K^+$-ATPase inhibitors; prostaglandins and prostaglandin analogs; laxatives; antidiarrheal agents; antiemetic agents; prokinetic agents; antiparasitic agents such as antimalarial agents, antibacterial agents, drugs for treatment of protozoal infections and antihelmintic drugs; antimicrobial drugs such as sulfonamides, quinolones, β-lactam antibiotics, aminoglycosides, tetracyclines, chloramphenicol and erythromycin; drugs for treatment of tuberculosis, drugs for treatment of leprosy; antifungal agents; antiviral agents; antineoplastic agents; immunomodulators; hematopoietic agents; growth factors; vitamins; minerals; anticoagulants; hormones and hormone antagonists such as antithyroid drugs, estrogens, progestins, androgens, adrenocortical steroids and adrenocortical steroid inhibitors; insulin; hypglycemic agents; calcium resorption inhibitors; clucocorticoids; retinoids and heavy-metal antagonists.

The annular body can be formed of any powdered or granular pharmaceutically acceptable excipients and can itself include a pharmaceutically active ingredient. In particular, it may be mentioned that diluents, binders, disintegrants, glidants, lubricants, flavorants, colorants and the like can be included in the annular body. Powdering and granulation with conventional excipients and the techniques for forming compressed bodies therefrom with given characteristics in terms of friability, hardness and freedom from capping is well within the knowledge of those skilled in the art of tableting.

Preferred excipients for forming the annular body include hydroxypropyl cellulose (e.g., Klucel™), hydroxypropyl methylcellulose (e.g. Methocel™), microcrystalline cellulose (e.g., Avicel™), starch, lactose, sugars, polyvinylpyrrolidone (e.g., Kollidon™, Plasdone™) and calcium phosphate.

Figure 1B:
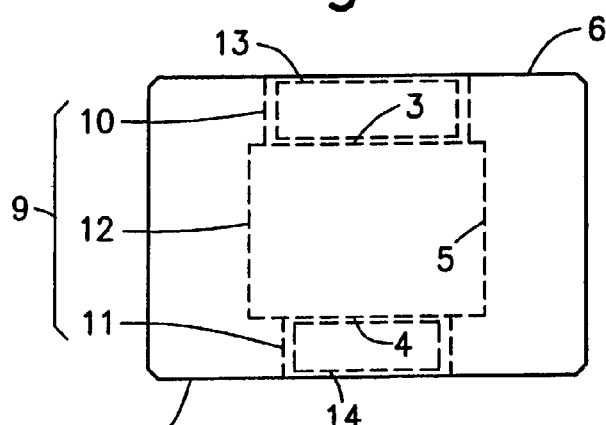
Figure 1C:
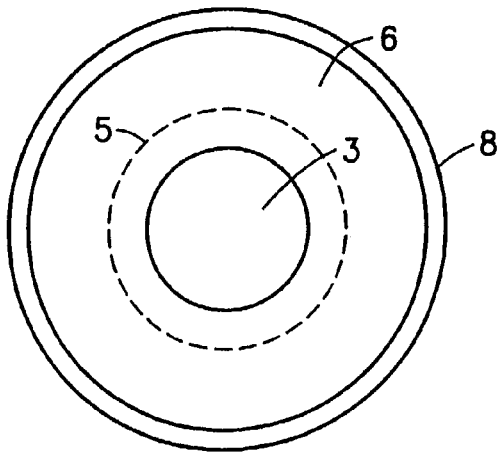

In an especially preferred compressed dosage form illustrated in FIG. 1, core tablet 1 containing the active pharmaceutical ingredient is recessed in the annular body 2, which is composed of non-ulcerative pharmaceutical excipients. The "recessed" tablet is especially well suited for oral delivery of ulcerative drugs. It reduces the incidence of pill esophagitis and contact gastritis by localizing the ulcerative drug in a core tablet that is shielded from contact with the mucosa lining the gastrointestinal tract. The drug is shielded because the core tablet is recessed. Recessing the core tablet does not significantly alter the release profile of the core tablet because a sizable portion of the surface of the core tablet is in fluid communication with the environment. In contrast, in coated or encapsulated dosage forms, the coating or capsule must be breached by gastric fluid before the drug is released. In the present invention, the outer contour of the dosage form protects the mucosa lining the gastrointestinal tract without interrupting fluid communication between the core tablet and the environment.

Exemplary of drugs that can be advantageously delivered using the preferred recessed dosage form of this invention are monosodium alendronate monohydrate, monosodium alendronate trihydrate, sodium etidronate, sodium risedronate, pamidronate, aspirin, ibuprofen, naproxen, fenoprofen, ketoprofen, oxaprozin, flubiprofen, indomethacin, sulindac, etodolac, mefenamic acid, meclofenamate sodium, tolmetin, ketorolac, diclofenac, piroxicam, meloxicam, tenoxicam, phenylbutazone and oxyphenbutazone.

Turning again to FIG. 1, core tablet 1 has opposed first and second surfaces 3 and 4 and an outer circumferential surface 5 extending between the opposed surfaces. Core tablet 1 is preferably cylindrical or disk shaped for ease of manufacture, but need not be so. In a dosage form for administration to humans, the maximum distance across either of the opposed surfaces 3 or 4 is preferably from about 2 mm to about 12 mm, more preferably from about 4 mm to about 7 mm, most preferably about 5 mm. Opposed surfaces 3 and 4 can be flat, concave or convex and are preferably flat for bearing modest axial compression forces exerted by flat pressing surfaces during formation of the annular body about the core tablet.

In outer contour, annular body 2 is preferably cylindrically shaped, but it can have any cross section, such as oval, elliptical or oblong. The outer diameter is preferably of from about 5 mm to about 15 mm, more preferably of from about 7 mm to about 12 mm, most preferably about 9 mm. The inner diameter can be any size up to about 2 mm less than the outer diameter. A narrow inner diameter less than 2 mm may slow release of the drug if an excipient in the annular body swells upon contact with gastric fluid. However, in some embodiments, a lower limit 0.5 mm may still be useful. Preferably, the inner diameter is 3 mm or greater.

Annular body 2 has opposed first and second annular faces 6 and 7, an outer circumferential surface 8 extending between the annular faces from their outer edges, and an inner circumferential surface 9 extending between the annular surfaces from their inner edges, thus defining an annulus.

As best seen in side view (FIG. 1B), inner circumferential surface 9 of annular body 2 consists of three longitudinal (axial) segments. First and second segments 10 and 11 are terminal and do not contact the sides of the core tablet. They are separated by an internal third segment 12 that contacts the outer circumferential surface 5 of core tablet 1. Opposed surfaces 3 and 4 of the core tablet are therefore recessed from annular faces 6 and 7 of the annular body. Opposed surfaces 3 and 4 are preferably recessed from about 0.5 mm to about 4 mm, more preferably about 1.5 mm relative to the annular faces 6 and 7 of the annular body (said recessed distance corresponding to the length of the corresponding terminal segment). The recess depth of surfaces 3 and 4 can be the same or it can be different.

By recessing the drug-containing core tablet, any contact between the dosage form and the gastrointestinal mucosa occurs with a surface of the annular body formed of non-ulcerative excipients, and optionally one or more non-ulcerative co-active ingredient, rather than with the solid ulcerative active ingredient. However, one or both of opposed surfaces 3 and 4 can be flush with annular faces 6 and 7 of the annular body without deleterious effect when the dosage form of the present invention is used to administer non-ulcerative drugs.

To better apprehend the preferred recessed dosage form embodiment of the invention, it is useful to conceive of surface 3 of the core tablet and first longitudinal segment 10 as defining a first void 13. Likewise, surface 4 of the core tablet and second longitudinal segment 11 define a second void 14. Voids 13 and 14 fill with gastric fluid when the dosage form is immersed in gastric fluid after reaching the stomach. Gastric fluid passes through the voids to contact the core tablet and the drug leaves through the voids after it is dissolved. Voids 13 and 14 are preferably from about 0.5 mm to about 10 mm, more preferably from about 3 mm to about 6 mm and most preferably about 4.5 mm in width (measured parallel to first or second opposed surfaces). Drug release, therefore, does not occur by an osmotic mechanism such as occurs with pierced dosage forms made using the apparatus of U.S. Pat. No. 5,071,607. Rather, in a large still fluid environment, drug concentration drops off roughly isotropically and exponentially by diffusion. In contrast, osmotic release of the drug product would produce a streaming flow that can cause locally high concentrations of the drug and osmotic agents at considerable distance from the tablet. Osmotic streams highly concentrated in an ulcerative drug are potentially irritating to the mucosa, just like the solid drug, particularly if the tablet is lodged in a fold in the gastrointestinal wall.

Opposed surfaces 3 and 4 of the core tablet are preferably substantially exposed, i.e. are not substantially covered by the annular body. "Substantially exposed" means that less than about 50% of each of the opposed surfaces is concealed or hidden from visual inspection by the annular body. A portion of opposed surfaces 3 and 4 can be concealed by the annular body because of differences between the diameter and shape of the core tablet and the diameter and shape of certain pressing portions of the tooling used to compress the annular body, as will become apparent from consideration of the description of the tooling aspect of the invention. Such differences may result in inner segment 12 being offset from terminal segments 10 and 11, which, themselves, can have different longitudinal cross sections, e.g. have different diameters, as depicted in FIG. 1. Alternatively, the cross section of the annulus defined by inner circumferential surface 9 can be uniform throughout its length. Although a portion of opposed surfaces 3 and 4 can be concealed by the annular body that is not necessarily the case.

The solid dosage forms with a drug-containing core tablet sheathed in a compressed annular body of non-ulcerative excipients can be produced using a novel toolset that constitutes a second aspect of the invention.

The toolset can be used in conjunction with conventional tablet presses such as rotary presses and reciprocating presses or with presses that have been specially designed and manufactured. Examples of commercially available rotary presses are the Manesty Express 25, the Kilian RUD or RTS series and comparable equipment. Examples of commercially available reciprocating presses are the Manesty F3 and comparable equipment made by Stokes, Kilian and Key Industries.

The principle elements of the toolset are a columnar punch and a punch assembly comprising an annular punch having an annulus (or bore), a core rod slidably engageable within the annulus of the annular punch, wherein the core rod is capable of movement between a retracted position and an extended position, the core rod being biased in the extended position. The columnar punch and punch assembly are sized and shaped to fit into the die bore of a rotary or reciprocating tablet machine.

Figure 2:
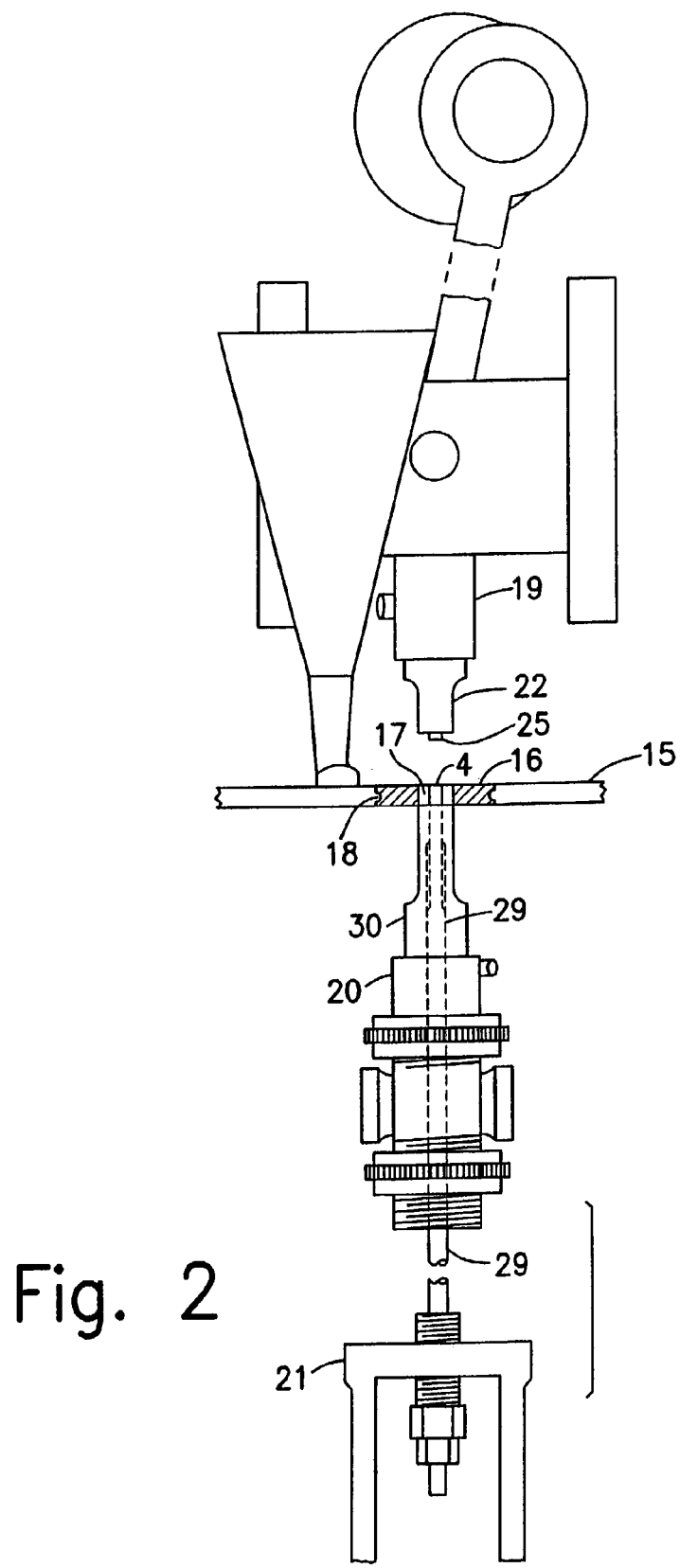
FIG. 2 is a perspective view of a single station tableting press shown with the toolset installed.

The toolset is well adapted for use with conventional single station tablet presses in which opposing upper and lower punches cooperatively compress a powder or granular material within a die. Referring to FIG. 2, single station presses are provided with a horizontal die table 15 having an aperture for receiving a die 16 and associated gripping means for locking the die into position. Dies for such presses customarily have opposed flat surfaces with a centrally located bore 17 having a highly polished wall surface extending from surface to surface and a circumferential locking groove 18 for engaging the gripping means. The bore serves as a receptacle for receiving powder or granular material to be compressed when the lower punch is partially inserted. The rims of the bore are customarily chamfered to help guide the punches into the bore. The bore's cross section determines the size and shape of the finished tablet in cross section. The quantity of material and pressure of compression determine the tablet's height. The bore can be cylindrical, but also can be any other shape.

In operation, the bore is filled with material and the upper punch is inserted into the bore and pressed against the material under high pressure thereby compressing the powder or granulated material into a tablet between the pressing, or contact, surfaces of the punches.

Together, the wall of the bore and the contact surfaces of the upper and lower punches define a mold that determines the size and surface contours of the final product. The final product can have any external contour by selection of appropriate bore shape and contact face contour.

After compression, the upper punch is withdrawn and the lower punch is advanced to eject the tablet.

The upper and lower punches are advanced and withdrawn by independently actuated upper and lower reciprocating rams 19 and 20. Customarily, single punch presses are also provided with a stationary mounting point 21 below the die table coaxial with the aperture.

A toolset of this invention adapted for use in a single station press comprises a columnar punch and a punch assembly comprising a collar, core rod and annular punch.

Referring now to FIG. 3, columnar punch 22 can be of a conventional columnar shape and is provided with locking means, such as locking flat 23 to secure it to the upper reciprocating ram 19 of the tablet press.

Columnar punch 22 includes a contact face 24. Contact face 24 can have any desired contour, e.g. standard concave, deep concave, extra deep concave, modified ball or flat. Preferably, the contour of contact face 24 is flat with a beveled edge.

A columnar punch for use in producing a dosage form of the present invention having a recessed core also has a protrusion 25 centrally located on the contact face 24, as illustrated. Preferably, the height of protrusion 25 is from about 0.5 mm to about 4 mm, more preferably about 1.5 mm. The shape of the protrusion is preferably cylindrical or tapered cylindrical but can also be oval, ellipsoid, oblong or any other shape desired. The protrusion is preferably cylindrical and has a flat raised surface 26. Protrusion 25 preferably has a diameter of from about 3 mm to about 7 mm, more preferably about 4.5 mm. In other embodiments, particularly suited to use when non-ulcerative active pharmaceutical ingredients are to be administered, protrusion 25 is absent.

Punch assembly 27 comprises collar 28, core rod 29 slidably engaged with collar 28 and annular punch 30 slidably engageable with core rod 29.

Collar 28 is provided with mounting means, such as external threads 31 around its circumference for mounting to stationary mounting point 21 located below the die table. As illustrated, the distal end 32 of collar 28 relative to the die table when installed, has a gripping section (shown with optional hexagonal cross section) for gripping by a wrench for mounting to stationary mounting point 21. At the proximal end 33 of the collar 28 relative to the die table when installed, the annulus is dimensioned to receive and guide the core rod 29.

Away from the proximal end of the collar, the diameter of the annulus is substantially greater than that of the core rod to provide a housing 34 for a biasing means such as spring 35. The coils of spring 35 encircle the core rod. Although a coil spring 35 is a preferred biasing means, biasing can be accomplished by other means, such as a sta.ck of Belleville washers or an elastic insert.

Spring 35 or other biasing means engages retaining ring 36 mated to core rod 29. Retaining ring 36 can be mated to the core rod by clamping engagement with a circumferential groove 37 in the rod. The retaining ring can be a conventional C-clip which engages the groove, or it can be a clamp or any other structure against which the biasing means can exert a biasing force and which is restrained from movement relative to core rod 29 in a direction parallel to the long axis of the core rod.

As illustrated, an annular locking bolt 38 engages internal threads 39 at the distal end of collar 32. The bore 40 through locking bolt 38 is dimensioned to receive and, in conjunction with the annulus at the proximal portion of the collar, to restrain motion of core rod 29 to axial movement. Locking bolt 38 also retains and can compress the biasing means. Core rod 29 is biased in the direction of the die table when the collar is installed on stationary mounting point 21 and is retained in slidable engagement with collar 28 by retaining ring 36 and locking bolt 38. The height of rod tip 41 is adjusted by advancing or retracting collar 28 relative to stationary mounting point 21, e.g. by rotating the collar when in threaded engagement with the stationary mounting point.

Core rod 29 can vary in diameter along its length. A preferred diameter of rod tip 41 is from about 0.5 mm to about 10 mm, more preferably about 4.5 mm. However, for rigidity, the core rod should be thicker, preferably from about 4 mm to about 12 mm throughout most of its length, more preferably about 9 mm. The rod can taper gradually from a narrow diameter at the tip to a larger shank diameter or it can change abruptly at a shoulder 42.

The core rod can be of two-piece construction. For instance, the core rod tip 41 could be adapted to attach to the core rod by providing external threads at its lower end and a socket with internal threads at the upper end of the core rod, or vice versa. A two-piece construction allows the core rod tip to be replaced if it is damaged or if a core rod tip of a different shape is desired. The core rod tip can have any desired diameter or shape.

Punch assembly 27 further comprises annular punch 30. Annular punch 30 is provided with means for attaching to lower reciprocating ram 20, such as locking flat 43. The bore 44 through annular punch 30 is dimensioned to receive and surround core rod 29 while permitting axial movement of annular punch 30 independent of the core rod. The bore through annular punch 30 can vary in diameter along the length of the punch providing an annular flange 45 for engagement with shoulder 42 on the core rod. Engagement of flange 45 with shoulder 42 prevents annular punch 30 and collar 28 from abutting each other during handling and installation. Annular punch contact surface 46 presses against the powder or granular material during compression. Contact face 46 can have any desired contour, e.g. standard concave, deep concave, extra deep concave, modified ball or flat. Preferably contact face 46 is flat with a beveled edge for ease of ejection of the finished tablet.

The columnar punch, annular punch, core rod and collar are preferably made of metal, more preferably steel, most preferably stainless steel.

In the final dosage form with recessed core tablet, the depth of first void 13 (FIG. 1) is determined by the height of protrusion 25. The depth of second void 14 is determined by the fill depth, strength of the bias on the core rod, the compressibility of the material and the thickness of the core tablet. These parameters can be adjusted by routine experimentation to control the depth of second void 14, which is suitably commensurate with the depth of first void 13.

In a second dosage form embodiment, either one or both of opposed surfaces 3 and 4 of the core tablet are flush with the annular faces 6 and 7 of the annular body 2. This alternative embodiment can be produced by using a columnar punch as previously described but lacking a protrusion 25. Surface 3 will generally be flush with annular face 6 if the columnar punch has a flat contact face. Whether the opposed surface 4 is flush with annular face 7 will depend on the fill depth, compressibility of the powder or granular material and thickness of the core tablet, which factors can be adjusted by routine experimentation to yield a dosage form with surface 4 recessed the desired distance relative to annular face 7.

To further illustrate the invention and the operation of the toolset, a cycle of operation will now be described. The cycle of operation is embodied in a process that constitutes a third aspect of the invention.

Figures 4A, 4B:
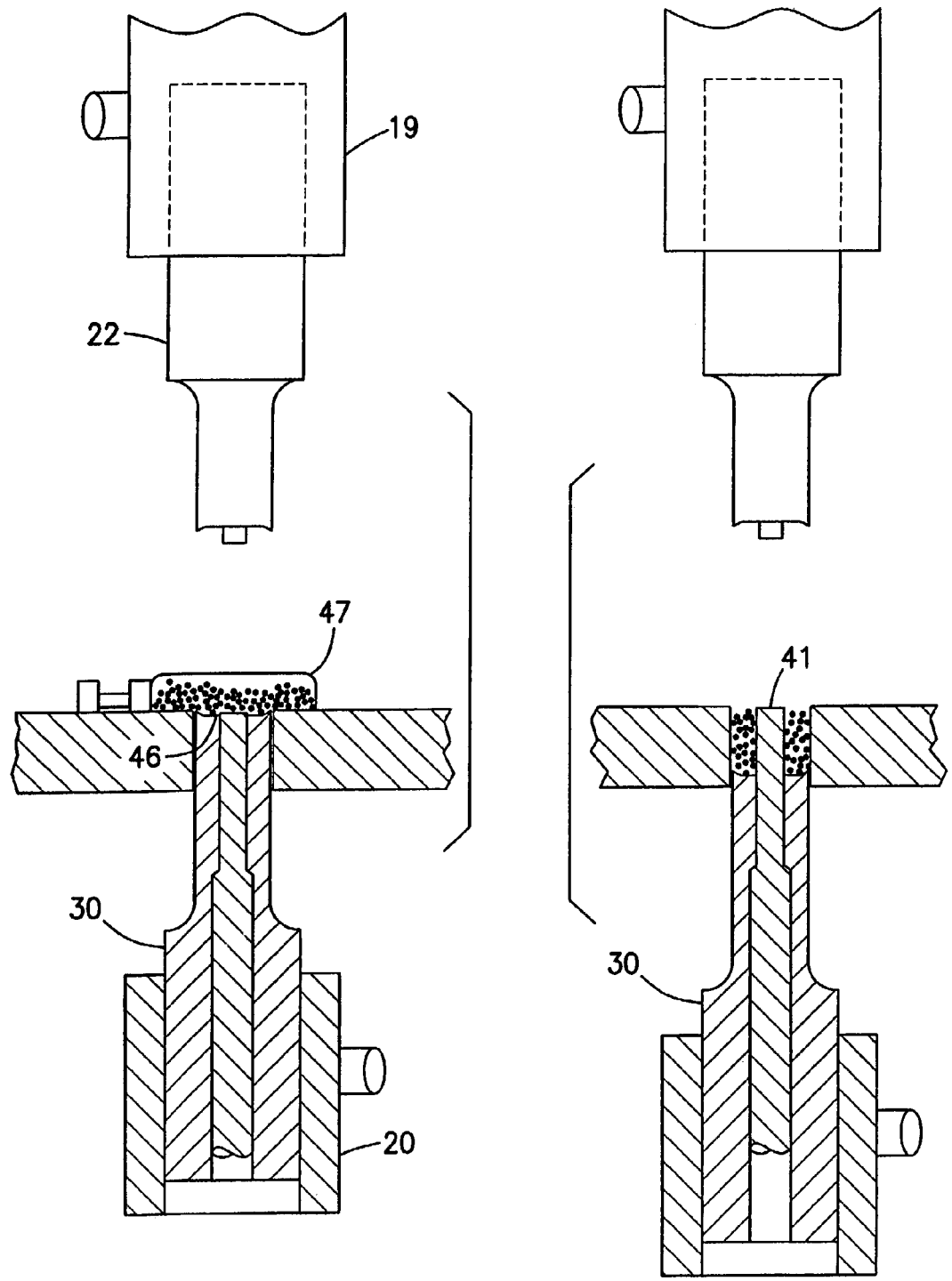

The cycle of operation is first illustrated on a single station press. The cycle begins with the first action that occurs after ejection of the tablet formed in a previous cycle. Referring now to FIG. 4a, feed shoe 47 moves laterally over the die bore while the annular punch 30 is in an advanced position such that contact surface 46 is substantially flush with the top surface of the die. In so doing, the feed shoe sweeps a finished tablet from atop the annular punch toward a chute leading to a receptacle where the tablets are collected. Annular punch 30 is retracted while the tip 41 of core rod 29 remains flush with the die surface (FIG. 4b). Retraction of the annular punch causes an annular cavity to form into which particles of the powder or granular material are fed from the feed shoe by gravity and/or pressure differential. Once the cavity is filled, the feed shoe is shifted away from the die bore.

Pre-compressed core tablet 1 is positioned atop the core rod using any conventional apparatus for producing tablets with a compressed coating such as that of a Kilian RUD press (FIG. 4*c*). The positioning means forms no part of the invention and has been omitted for clarity.

Columnar punch 22 is advanced by upper reciprocating ram 19 (FIG. 4*d*). As columnar punch 22 approaches the bore, the raised surface 26 of protrusion 25 presses upon core tablet 1. As columnar punch 22 enters bore 17, core tablet 1 is pushed into the bore by the protrusion against the biasing force exerted on core rod 29. Continued movement of columnar punch 22 into the die bore compresses the powder or granular material into an annular body around the core tablet. Strong compressive forces can be exerted on the powder or granular material without breaking the core tablet because the core tablet travels into the bore before the powder or granular material is fully compressed.

Those skilled in the art may also appreciate that protrusion 25 could be replaced with a core rod in the columnar punch that is biased toward an extended position so that the tip of the rod would press against core tablet 1 during compression. Such a core rod for the columnar punch would not necessarily be attached to a stationary mounting point on the press. It would be biased with greater force than core rod 29 so that pressure exerted by the columnar punch would push the core tablet into the bore against the resistance of the core rod.

Figure 4E:
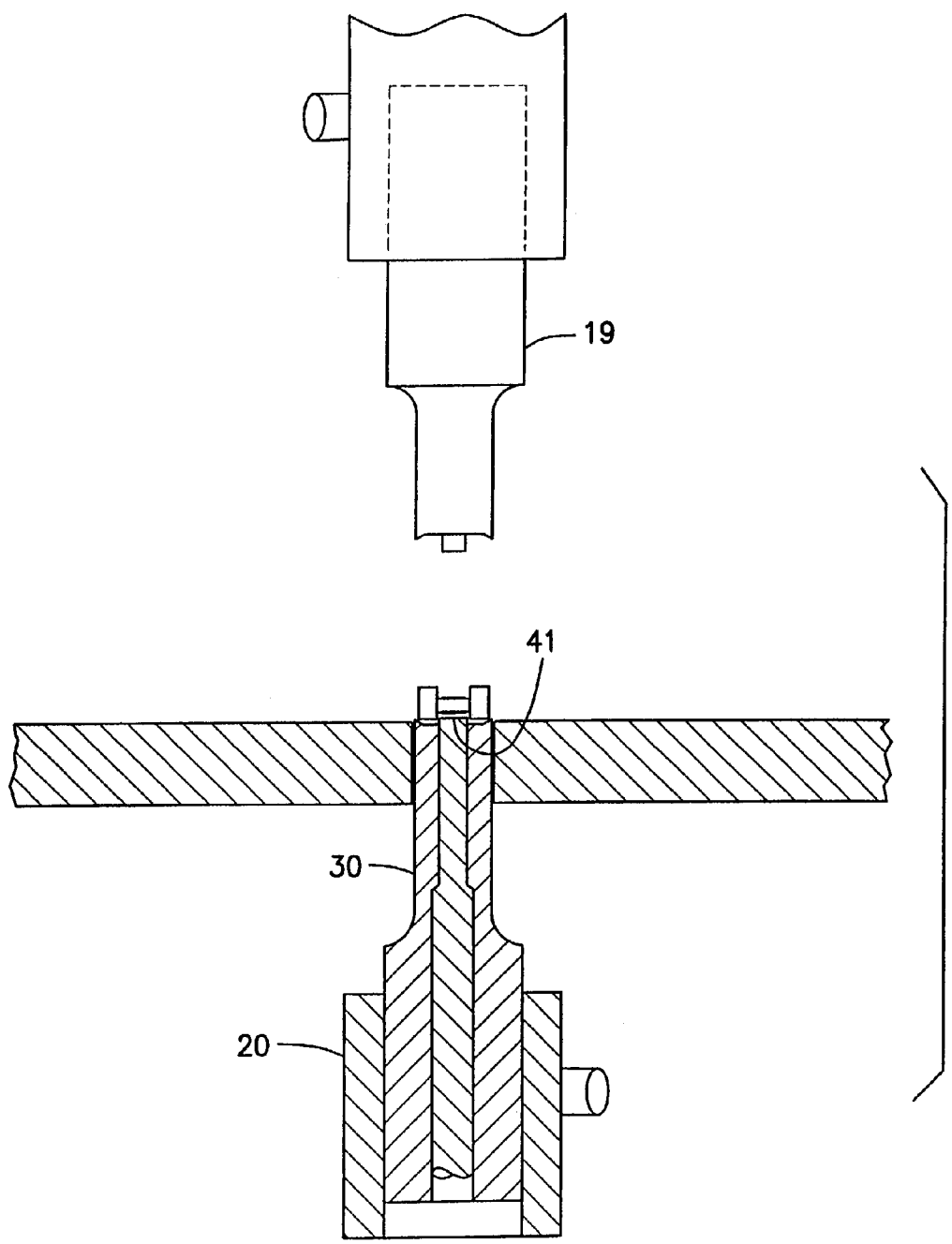

After the powder or granular material is compressed, the columnar punch is withdrawn. Either concurrently or subsequently, annular punch 30 is advanced by lower reciprocating ram 20 to a position such that contact face 46 is substantially flush with the upper surface of the die to elevate the finished tablet above the die where it can be swept from the die table in a subsequent cycle of operation (FIG. 4*e*). Meanwhile, the core rod is biased back to its original position flush with the die surface.

The toolset is well adapted for use in a rotary tablet press. The cross-sectional dimension and shape of the columnar punch, and the dimensions and shape of the protrusion (if present) are the same as in a punch adapted for use in a reciprocating tablet press. The other dimensions of the toolset are generally dictated by the dimensions and layout of a particular tableting press. These dimensions can be readily determined by those skilled in the art. The cross-sectional dimensions and shape of the annular punch and of the core rod are the same as in a punch adapted for use in a reciprocating tablet press, again with other dimensions being dictated by the dimensions and layout of a particular tableting press. These dimensions can be readily determined by those skilled in the art. In addition, the punches include conventional bearing surfaces at the end distal to their contact surfaces for engaging the cams and rollers that control their motion along the axis of the die bore, such as those shown in the patents that are incorporated by reference below.

In an annular punch for use in a rotary machine, the core rod biasing means preferably is housed in the annular punch and includes a means for adjusting the degree of extension of the core rod and/or the bias, such as a set screw or similar device.

Conventional rotary tablet presses are well known in the art. Some rotary presses and improvements related thereto are described in U.S. Pat. Nos. 5,462,427, 5,234,646, 5,256,046 and 5,635,223, which are incorporated herein by reference in their entirety. Rotary presses have a moving die table that rotates around a vertical axis. Mounted above and below the die table are upper and lower punch carriers that rotate synchronously with the die table. The punch carriers can be generally drum shaped bodies of about the same diameter as the die table or they can have arms that extend outward from a lesser diameter ring. The punch carriers are provided with a plurality of vertical holes or slots at regular intervals around their circumference or through the ends of the arms. When the press is in operation, punches are inserted into each slot with their contact faces pointing toward the die table. Each punch has a bearing means at the end opposite the contact face. The bearing means engage stationary cams and rollers which control the vertical motion of each punch during a cycle of operation. The cams and rollers are arranged such that in a cycle of operation, a powder or granular material is fed into a die while the lower punch is inserted into the die. Pressure is applied to the powder or granular material to produce a compressed body. After compression, one or more of the punches is removed from the die and the dosage form is released. Rotary presses are especially suited for high volume production because they typically contain numerous punch and die sets operating simultaneously.

A cycle of operation using the toolset of this invention adapted for use in a rotary press will now be described. As the die table rotates, one of the dies passes under a fill shoe or force feeder. While the die is passing underneath the shoe or feeder, the annular punch is withdrawn by the cam. The core rod remains in an extended position, up to the upper die face. The annular space left by withdrawl of the annular punch is filled with powder or granulate. At the next station, a core tablet is inserted onto the tip of the core rod by conventional means, such as those used in "press coat" machines like the Kilian RUD. The core tablet can be positioned atop the core rod by any method. On further rotation, the die comes to the compression station where the columnar punch with, or without, its protrusion moves downward and pushes the core tablet into the bed of powder or granular material. The force of the columnar punch retracts the core rod against the bias and the powder or granular material is compressed into an annular shape around the core tablet. In the dosage form product, one recess is defined by the height of the protrusion and the other recess is defined by a combination of the factors such as the strength of the bias, the fill depth, the compactability of the powder or granular material and the thickness of the core tablet. After the powder is compressed, the die rotates further to where the columnar punch is withdrawn from the die. Either concurrently or subsequently, the annular punch is raised until it reaches the die face. The core rod rises concurrently to the die face due to the bias. The tablet is swept out of the die by an ejection element and is collected.

While reference has been made to "upper" and "lower" elements in the description of the toolset and process for making solid dosage form according to the invention, the spacial relationships of the elements are determined by the design and construction of the press in which they are used. Use of the terms "upper" and "lower" is not intended to limit the invention to a vertical arrangement of the elements.

Having thus described the present invention with reference to certain preferred embodiments, the invention will now be further illustrated by the following example.

EXAMPLE

This example summarizes a study designed to determine the rate and extent of absorption of alendronate sodium in human subjects upon administration of a solid pharmaceutical dosage form of the present invention ("protected tablet").

Materials and Methods

Protected tablets were made as follows.

Tablet Core: 85.4 g of alendronate trihydrate (TEVA Assia Ltd.) and 2.6 g of xylitol (Danisco Sweeteners OY) were granulated with 20 g water in a Diosna (model P1/6) granulator for 3 min. The granulate was dried at 40° C. for one hour in a fluidized bed dryer and milled through a 0.8 mm screen. The granulate was blended with 11 g crospovidone NF (BASF Pharma) for five minutes. One gram magnesium stearate NF/EP (Mallinkrodt Inc.) was added and the granulate was further blended for an additional 0.5 minutes. The blend was compressed using a Manesty F3 single punch tablet machine fitted with a 5 mm flat beveled punch. The tablet weight was 94.9 mg±1.0% RSD. The hardness of the core tablets was 3-6 kP.

Protected Tablets: A mixture of 94 grams compressible sucrose (Nutab™, DMV International) and 5 grams microcrystalline cellulose (Avicel™ pH102,FMC International) were blended for five minutes. One gram magnesium stearate (NF/EP, Mallinkrodt Inc.) was added and the mixture was blended for another half a minute.

A Manesty f3 single punch tableting machine was fitted with a spring-biased columnar punch and punch assembly constructed in accordance with the present invention. The core rod was designed for a 5 mm round core tablet and the die and punches for the outer tablet were designed to produce a round, 9 mm diameter, flat beveled solid pharmaceutical dosage form. The upper punch had a protrusion of diameter 4.5 mm and 1.2 mm height. The tablet press was operated and the protected tablets were produced. The tablet weight was 474 mg±0.62% RSD and the hardness of the protected tablets was 12-15 kP. The alendronate trihydrate content, expressed as alendronic acid was 66.8 mg±1.38% RSD (82.4 mg alendronate trihydrate being equivalent to 70 mg alendronic acid).

The drug-containing inner tablet was recessed from the surface of the annular body by about 1 mm.

Pharmacokinetic Study

A clinical trial involving twelve (12) human volunteers was conducted to demonstrate the pharmacokinetics of a solid dosage form of the present invention containing 70 mg alendronate. Its pharmacokinetics was compared to that of a commercial 70 mg Fosalan™ tablet of the prior art (Merck, Sharpe & Dohme).

Method

The study was a randomized, open-label, 2-treatment, 2 period, 2 sequence crossover design under fasting conditions. Twelve (12) healthy adult male volunteers, 18-55 years of age were the subjects in the study.

The study was divided into first and second study periods, each of 36 hours duration, with a 14 day "wash-out" period between the study periods. All subjects who completed both study periods were included in the analysis. Subjects were randomly assigned to two groups. One group was administered alendronate via the protected tablet in the first period and administered control Fosalan in the second period. The order of administration to the second group was reversed.

In both periods, alendronate was administered in the fasted state. A standardized meal was provided 4 hours after administration. Snacks were provided on a standardized schedule that was the same for all subjects in both study periods. Water was provided ad libitum. In addition, subjects were encouraged to drink at least 200 ml of water at regular intervals during each study period.

The bioavailability of alendronate was determined by measuring the cumulative levels of alendronate excreted in the urine over a 36 hour period following oral ingestion of the test and control tablets (hereafter "$Ae_{0-36}$"). An initial (t=0) urine sample was taken immediately after administration. Urine samples were taken at 11 regularly scheduled points in time over the 36 hour test period. All urine samples were analyzed for alendronate using a validated HPLC-FLR assay.

Results

The main pharmacokinetic parameters obtained from the analyses of urine samples are collected in Table 1.

TABLE 1

Pharmacokinetic Parameters

| Parameter | Administration via Protected Tablet | | | Administration via Fosalan (control) | | |
| --- | --- | --- | --- | --- | --- | --- |
|  | Mean | ±SD | CV (%) | Mean | ±SD | CV (%) |
| $Ae_{0-36}$ (µg) | 113.6 | 77.2 | 67.9 | 102.6 | 36.8 | 36.8 |
| $R_{max}$ (µg/h) | 37.9 | 19.9 | 51.5 | 31.7 | 11.8 | 38.3 |
| $T_{max}$ (h) | 1.4 | 0.9 | — | 1.4 | 0.9 | — |

A comparison of the pharmacokinetic parameters of the dosage form in accordance with this invention with the pharmacokinetic parameters of the prior art dosage form is provided in Table 2.

TABLE 2

Comparison of Pharmacokinetics of the Protected Tablet to Prior Art

|  | $Ae_{0-36}$ (mg) | $R_{max}$ (mg/h) |
| --- | --- | --- |
| Geometric Mean of Ratio | 0.99 | 1.12 |
| 90% Geometric C.I. | 75.31% to 128.79% | 93.98% to 135.01% |
| Intra-subject C.V. | 37.48% | 24.85% |

Figure 5:
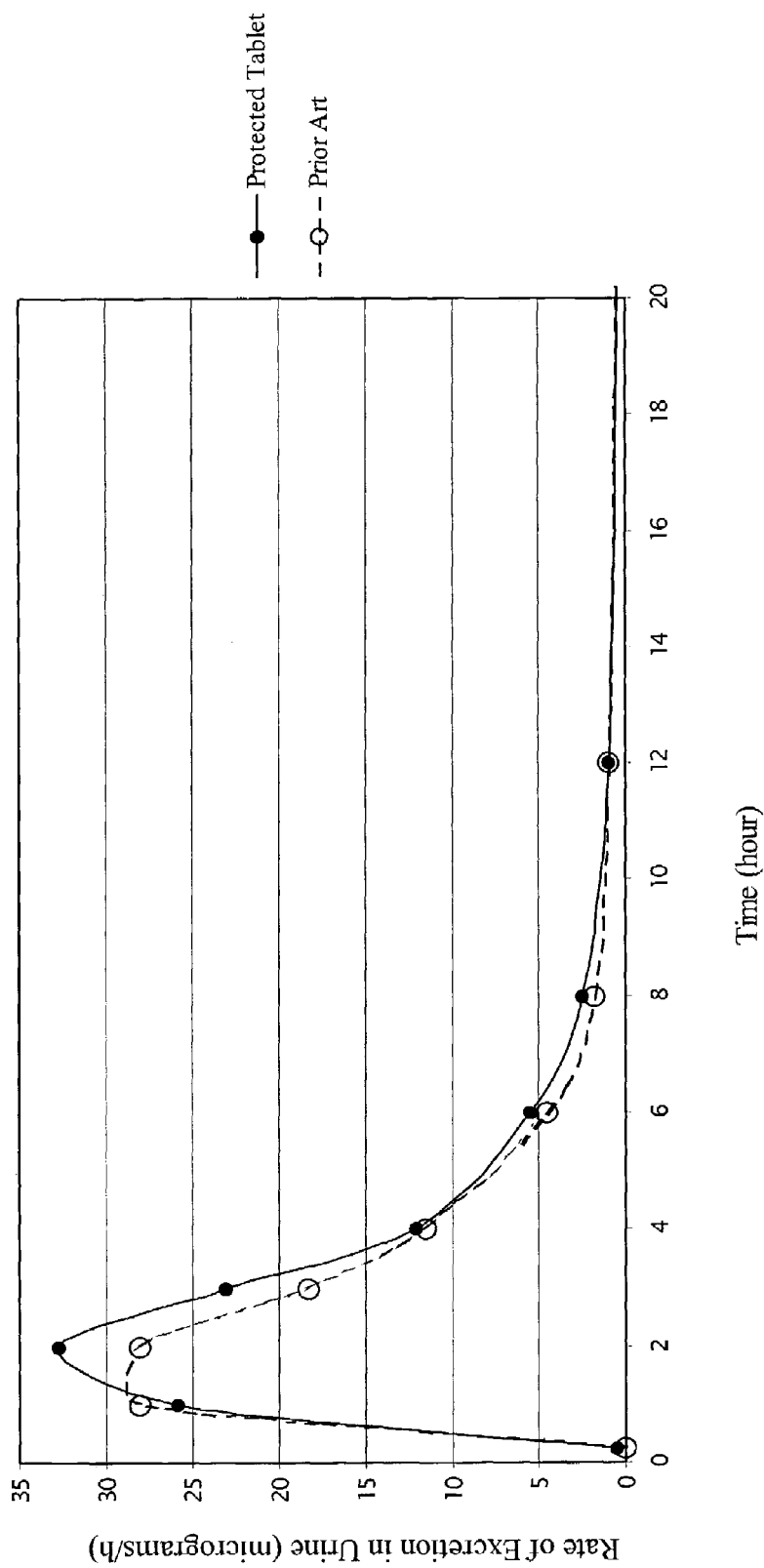
FIG. 5 is a plot of the average rate of alendronate excretion in urine of humans who had taken a dosage form in accordance with the present invention containing 70 mg monosodium alendronate and a prior art 70 mg monosodium alendronate dosage form.

By reference to Tables 1 and 2, and FIG. 5, one can see that alendronate administered via the solid dosage form of the present invention gives essentially the same pharmacokinetic results as administration via Fosalan. The total amount of the alendronate excreted into urine over 36 hours is essentially the same for both treatments with the maximum rates of excretion (parallel to $C_{max}$ in a pharmacokinetic study of plasma levels of drug) also close.

The profile of excretion into urine was similar for all subjects and in both treatments. The majority of the subjects had their maximum rate of excretion ($R_{max}$) between one and two hours. For five of the subjects, the $R_{max}$ occurred earlier than 1 hour after administration when they took Fosalan. Four of the subjects experienced a $R_{max}$ in less than an hour when they took the protected tablet. One of the subjects had an $R_{max}$ in the third hour when he took Fosalan while two of the subjects had a $R_{max}$ in the third hour when they took the protected tablet.

The total amount of excreted alendronate ranged from 36.9 µg to 158.6 µg when Fosalan was administered and from 30.1 µg to 284.4 µg when the solid oral dosage form of the present invention was administered. In only two subjects was there a greater than two fold difference between the total amount of excreted alendronate between the two treatments. Another subject excreted a very low amount of alendronate regardless of how the alendronate was administered.

The bioavailability of alendronate administered via the novel solid dosage form of the present invention in equivalent to that of alendronate administered by dosage forms of the prior art. However, the dosage form of the prior art does not provide any protection against contact of the alendronate with the mucous membranes of the esophageous and stomach while the bioequivalent novel dosage form of the present invention affords such protection.

Having thus described the invention with reference to certain preferred embodiments, other embodiments will be apparent from this description to those skilled in the art to which the invention pertains. It is intended that the specification is considered exemplary only, with the scope and spirit of the invention being indicated by the claims which follow.

What is claimed is:

1. A solid pharmaceutical dosage form for oral administration to a patient, comprising:
    a recessed core tablet having a substantially exposed first surface and a substantially exposed second surface and an outer surface extending between the exposed first and second opposed surfaces, wherein the first and second substantially exposed surfaces are opposed one to the other, and the substantially exposed surfaces are exposed to the dosage form external environment;
    the core tablet containing an active pharmaceutical ingredient; wherein
    the core tablet is sheathed in an annular body of compressed powder or compressed granular material that encircles the core tablet, and is in contact with the outer surface of the core tablet, leaving the opposed surfaces of the core tablet substantially exposed;
    the annular body having opposed first and second annular faces, an outer surface extending between the annular faces outer edges, and an inner surface extending between the annular faces inner edges, thereby defining an annulus; and wherein
    the substantially exposed first and second opposed surfaces of the core tablet are both recessed with respect to the annular faces of the annular body, such that, prior to and following oral administration, the recessed surfaces of the core tablet are shielded from contact with the mucosa lining the gastrointestinal tract.

2. The solid pharmaceutical dosage form of claim 1, wherein the active pharmaceutical ingredient is released into the annulus of the annular body.

3. The solid pharmaceutical dosage form of claim 2, wherein the active pharmaceutical ingredient is ulcerative.

4. The solid pharmaceutical dosage form of claim 3, wherein the active pharmaceutical ingredient is a bisphosphonate or NSAID.

5. The solid pharmaceutical dosage form of claim 4, wherein the active pharmaceutical ingredient is selected from the group consisting of monosodium alendronate monohydrate, monosodium alendronate trihydrate, sodium etidronate, sodium risedronate, pamidronate, asprin, ibuprofen, naproxen, fenoprofen, ketoprofen, oxaprozin, flubiprofen, indomethacin, sulindac, etodolac, mefenamic acid, meclofenamate sodium, tolmetin, ketorolac, diclofenac, piroxicam, meloxicam, tenoxicam, phenylbutaxone, and oxyphenbutazone.

6. The solid pharmaceutical dosage form of claim 1, wherein the core tablet comprises sodium alendronate.

7. The solid pharmaceutical dosage form of claim 5, wherein the active pharmaceutical ingredient is monosodium alendronate monohydrate.

8. The solid pharmaceutical dosage form of claim 5, wherein the active pharmaceutical ingredient is monosodium alendronate trihydrate.

9. The solid pharmaceutical dosage form of claim 1, wherein the core tablet is recessed from about 0.5 mm to about 4 mm.

10. The solid pharmaceutical dosage form of claim 1, wherein the annular body contains an active ingredient.

11. The solid pharmaceutical dosage form of claim 1, wherein the powder or granular material includes a pharmaceutical excipient selected from the group consisting of hydroxypropyl cellulose, hydroxypropyl methylcelullose, microcrystalline cellulose, starch, lactose, sugars, polyvinylpyrrolidone, and calcium phosphate.

12. The dosage form of claim 1, wherein the distance across each of the opposed surface of the core tablet is from about 2 mm to about 12 mm.

13. The dosage form of claim 1, wherein the distance across each of the opposed surfaces of the core tablet is from about 4 mm to about 7 mm.

14. The dosage form of claim 1, wherein the inner surface of the annular body consists of a first and second terminal segment and one internal segment, further wherein the first terminal segment and the opposed first surface of the core tablet define a first void and the second terminal segment and the opposed second surface of the core tablet define a second void and further wherein the distance across each of the voids is from about 0.5 mm to about 10 mm.

15. The dosage form of claim 14, wherein the distance across each void is from about 3 mm to about 6 mm.

16. The dosage form of claim 1 wherein the core tablet is in the shape of a disk or cylinder.

17. The solid dosage form of claim 1, wherein the first opposed surface of the core tablet is recessed to an extent different from the second opposed surface.

18. The solid dosage form of claim 1, wherein the cross-section of the core tablet is uniform.

19. The solid pharmaceutical dosage form of claim 18, wherein the cross-section of the core tablet is cylindrical.

20. A process for producing a the solid pharmaceutical dosage form of claim 1, comprising forming the annular body of powder or granular material around the core tablet by compression.

21. The process of claim 20, wherein forming the annular body comprises:
    a) filling an annular cavity with the powder or granular material, the annular cavity being defined by:
        i) the bore of die,
        ii) an annular punch partially inserted into the bore from one side,
        iii) a core rod in an extended position wherein it extends through the bore and the annular punch with its tip substantially flush with the surface of the die on the side opposite the annular punch, wherein the core rod is movable between the extended position and a retracted position wherein the tip is inside the bore, and further wherein the core rod is biased in the extended position,
    b) placing the core tablet at the tip of the core rod, and
    c) advancing a columnar punch toward the bore from the side of the die opposite the annular punch, thereby pushing the core tablet into the bore against the bias force on the core rod and causing the core rod to retract, and compressing the powder or granular material around the core tablet, forming the annular body.

22. The process of claim 21, wherein the columnar punch contact face has a centered protrusion.

23. The process of claim 21, further comprising withdrawing at least one of the punches from the die bore after advancing the columnar punch toward the bore and ejecting the solid pharmaceutical dosage form from the bore.

24. The process of claim 20, wherein the compression step comprises compression on or in a tablet press equipped with the following parts and tooling:

a die table mounting a die with a bore extending therethrough, a columnar punch mounted on one side of the die table coaxially with the bore and movable along the axis of the bore with the end proximal to the die table sized to be received into the bore and being terminated with a contact face for pressing against the powder or granular material, an annular punch mounted on the other side of the die table coaxially with the bore and moveable along the axis of the die bore independently of the columnar punch, wherein the end of the annular punch proximal to the die table is sized to be received into the die bore and is terminated with a contact face for pressing against the powder or granular material, and a core rod slidably engaged within the annulus of the annular punch and aligned coaxially with the die bore, the core rod moveable between a retracted position and an extended position wherein the core rod extends through the die bore with the tip of the rod substantially flush with the surface of the die, the core rod being biased to the extended position by biasing means, and wherein forming the annular body comprises:

a) filling an annular cavity with the powder or granular material, the annular cavity being defined by the die bore, the core rod in its extended position, and the contact face of the annular punch partially inserted into the bore, b) placing the core tablet at the tip of the extended core rod, c) advancing the columnar punch, whereby the core tablet is pushed into the die bore against the bias force exerted by the core rod biasing means, whereby the core rod at least partially retracts, and whereby the powder or granular material is compressed between the contact faces of the columnar and annular punches, forming the annular body.

25. The process of claim 24, further comprising withdrawing at least one of the punches from the die bore after advancing the columnar punch toward the bore and ejecting the solid pharmaceutical dosage form from the bore.

26. The process of claim 24, wherein the columnar punch contact face has a centered protrusion.

27. The process of claim 24, wherein the die table is horizontal, the columnar punch is above the die table, and the annular punch is below the die table, wherein the tablet press is further equipped with a feed shoe for delivering the powder or granular material to the die bore from above and a collar fixedly mounted below the die table coaxially with the die bore, the core rod being slidably engaged within the annulus of the collar and biased by bias means housed in the collar, and wherein, the annular cavity is filled from the feed shoe, the columnar punch is withdrawn after the advancing step and the solid pharmaceutical dosage form is ejected from the bore by advancing the annular punch into the bore.

28. The process of claim 27, wherein the annular cavity is filled by placing the feed shoe over the die bore while the annular punch is positioned with its contact face approximately flush with the die surface and then lowering the lower punch to form the cavity and drawing the powder or granular material into the cavity by gravity or pressure differential.

29. The process of claim 20, wherein the compression step comprises compression on or in a tablet press equipped with the following parts and tooling:

a generally planar and circular die table capable of rotation about an axis normal to the plane and having a plurality of bores therethrough around its circumference at regular intervals, a first punch carrier mounted on one side of the die table and a second punch carrier mounted on the other side of the die table, each punch carrier rotating about the axis synchronously with the die table and provided with a plurality of vertical holes or slots, each hole or slot being in registry with a bore through the die table, a plurality of annular first punches, each slidably engaged within one of the vertical holes or slots of the first punch carrier, each of the first punches having an end proximal to the die table sized to be received into a bore and being terminated with an annular contact face for pressing against the powder or granular material, each of the first punches further having a core rod slidably engaged within the annulus and aligned coaxially with a die bore, the core rod moveable between a retracted position and an extended position wherein the core rod extends through the die bore with the tip of the rod substantially flush with the surface of the die table, the core rod being biased to the extended position by biasing means, a plurality of second punches, each slidably engaged within one of the vertical holes or slots of the second punch carrier, each of the second punches having an end proximal to the die table sized to be received into a bore and terminated with a contact face for pressing against the powder or granular material, and means for controlling the motion of the punches in the direction of the axis, and wherein forming the annular body comprises:

a) filling an annular cavity with the powder or granular material, the annular cavity being defined by a die bore, a core rod in its extended position and the contact face of a first punch partially inserted into the bore, b) placing the core tablet at the tip of the extended core rod, c) advancing a second punch into the die bore, whereby the core tablet is pushed into the die bore against the bias force exerted by the core rod biasing means, whereby the core rod at least partially retracts, and whereby the powder or granular material is compressed between the contact faces of the first and second punch, forming the annular body.

30. The process of claim 29, further comprising withdrawing at least one of the punches from the die bore after advancing the second punch toward the bore and ejecting the solid pharmaceutical dosage form from the bore.

31. The process of claim 29, wherein the second punch contact face has a centered protrusion.

32. The process of claim 29, wherein the annular cavity is filled by rotating the die table under a feed shoe while the first punch is positioned with its contact face substantially flush with the die table surface and then retracting the first punch to form the cavity and drawing the powder or granular material into the cavity by gravity or pressure differential.

* * * * *

UNITED STATES PATENT AND TRADEMARK OFFICE
CERTIFICATE OF CORRECTION

PATENT NO. : 7,611,722 B2
APPLICATION NO. : 10/419536
DATED : November 3, 2009
INVENTOR(S) : Lerner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 41 days.

Signed and Sealed this

Fourteenth Day of December, 2010

David J. Kappos
*Director of the United States Patent and Trademark Office*